US011993879B2

(12) United States Patent
Niedt et al.

(10) Patent No.: US 11,993,879 B2
(45) Date of Patent: May 28, 2024

(54) ADHESIVE PATTERN RESIDING ON A MOVING BASE WEB

(71) Applicant: Kimberly-Clark Worldwide, Inc., Neenah, WI (US)

(72) Inventors: James Niedt, Grand Chute, WI (US); Walter Hagy, Martinez, GA (US); Kyle Barriger, Neenah, WI (US); Joe Sina, Freedom, WI (US); Daniel J. Grassl, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 662 days.

(21) Appl. No.: 16/622,693

(22) PCT Filed: Jun. 23, 2017

(86) PCT No.: PCT/US2017/039088
§ 371 (c)(1),
(2) Date: Dec. 13, 2019

(87) PCT Pub. No.: WO2018/236397
PCT Pub. Date: Dec. 27, 2018

(65) Prior Publication Data
US 2020/0113744 A1 Apr. 16, 2020

(51) Int. Cl.
*D04H 1/62* (2006.01)
*D04H 1/593* (2012.01)
*A61F 13/15* (2006.01)

(52) U.S. Cl.
CPC ............... *D04H 1/62* (2013.01); *D04H 1/593* (2013.01); *A61F 2013/1591* (2013.01); *Y10T 428/24802* (2015.01); *Y10T 428/24826* (2015.01)

(58) Field of Classification Search
CPC .... D04H 1/593; D04H 1/62; A61F 13/15804; A61F 2013/1591; Y10T 428/24802; Y10T 428/24826; B05D 5/10
See application file for complete search history.

(56) References Cited

U.S. PATENT DOCUMENTS

| 3,926,148 | A | 12/1975 | Honsel |
| 4,020,194 | A | 4/1977 | McIntyre et al. |

(Continued)

FOREIGN PATENT DOCUMENTS

| EP | 0 232 578 A2 | 8/1987 |
| EP | 0 878 277 A3 | 11/1999 |

(Continued)

OTHER PUBLICATIONS

ARC International, "Print Cylinders", http://www.arcinternational.com/products/corrugated-printing-products; 2 pages.

(Continued)

*Primary Examiner* — Gerard Higgins
(74) *Attorney, Agent, or Firm* — Dority & Manning, P.A.

(57) ABSTRACT

A unique and distinctive adhesive pattern is applied to a base web, such as a nonwoven web. The adhesive pattern can include a plurality of treated discrete areas that can extend parallel in the longitudinal direction of the web. Each treated discrete area can include a head portion connected to a tail portion. The head portion, in one embodiment, can have a greater amount of adhesive composition based on mass per area in relation to the amount of adhesive composition contained in the tail portion. The overall length of the treated discrete area can be relatively short in relation to adhesive patterns produced in the past using conventional slot coating processes. The adhesive pattern provides a secure attachment to an adjoining material and can provide various processing advantages.

22 Claims, 5 Drawing Sheets

(56) References Cited

U.S. PATENT DOCUMENTS

| | | |
|---|---|---|
| 4,081,301 A | 3/1978 | Buell |
| 4,371,571 A | 2/1983 | McIntyre et al. |
| 4,547,243 A | 10/1985 | Brody |
| 4,608,115 A | 8/1986 | Schroth et al. |
| 5,049,122 A | 9/1991 | Marschke |
| 5,363,728 A | 11/1994 | Elsner et al. |
| 5,494,237 A | 2/1996 | Summey, III |
| 5,524,828 A | 6/1996 | Raterman et al. |
| 5,738,669 A * | 4/1998 | Suzuki .................. C09J 123/10 604/389 |
| 5,762,596 A | 6/1998 | Dittli |
| 5,779,854 A | 7/1998 | Sandmeier |
| 6,394,161 B1 | 5/2002 | Kakishima et al. |
| 6,730,011 B2 | 5/2004 | Tokiwa et al. |
| 6,733,284 B2 | 5/2004 | Butsch et al. |
| 6,758,923 B2 | 7/2004 | Butterworth et al. |
| 6,779,788 B2 | 8/2004 | Takahashi et al. |
| 6,881,471 B2 | 4/2005 | Toussant et al. |
| 6,895,649 B2 | 5/2005 | Kojo et al. |
| 6,942,610 B2 | 9/2005 | St. Germain et al. |
| 6,978,816 B1 | 12/2005 | Byrne et al. |
| 7,163,133 B2 | 1/2007 | Woody et al. |
| 7,875,197 B2 | 1/2011 | Whitesides et al. |
| 8,166,858 B2 | 5/2012 | Luquette |
| 8,303,759 B2 | 11/2012 | Baldauf |
| 8,491,742 B2 | 7/2013 | Waas et al. |
| 9,050,213 B2 | 6/2015 | LaVon et al. |
| 9,289,967 B2 | 3/2016 | Ordway et al. |
| 2005/0137549 A1 | 6/2005 | Lindsay et al. |
| 2007/0065574 A1 | 3/2007 | Rosati et al. |
| 2008/0229953 A1 | 9/2008 | Saito et al. |
| 2012/0184933 A1* | 7/2012 | Floeter .............. A61F 13/15699 156/60 |
| 2013/0240122 A1* | 9/2013 | Adams .............. A61F 13/15577 156/60 |
| 2013/0260031 A1 | 10/2013 | Sakaue |
| 2015/0083309 A1 | 3/2015 | Long et al. |
| 2016/0265165 A1 | 9/2016 | Proctor, Sr. |

FOREIGN PATENT DOCUMENTS

| | | |
|---|---|---|
| EP | 1 547 553 A2 | 6/2005 |
| JP | H0833677 A | 2/1996 |
| JP | 2010/279938 A | 12/2010 |
| JP | 2013/215580 A | 10/2013 |
| KR | 20060063214 A | 6/2006 |
| RU | 2 170 241 C2 | 7/2001 |
| WO | WO 2018/236395 | 12/2018 |

OTHER PUBLICATIONS

H.B. Fuller, "Where Adhesive Innovation and Tissue and Towels Comet Together", http:/www.hbfuller.com/tissue-towel, 5 pages.
International Search Report and Written Opinion for PCT/US2017/039088, dated Feb. 23, 2018, 13 pages.
Korean Office Action Corresponding to Application No. 1020207000144 dated May 3, 2021.

* cited by examiner

ADHESIVE PATTERN RESIDING ON A MOVING BASE WEB

RELATED APPLICATIONS

The present application is based upon and claims priority to PCT International Patent Application No. PCT/US2017/039088, filed on Jun. 23, 2017, which is incorporated herein by reference.

BACKGROUND

Absorbent articles, such as disposable diapers, training pants, adult incontinence articles and the like, generally include several different components which are adhesively bonded together. For example, adhesive has been used to bond individual layers of the absorbent article, such as the outer cover and body side liner, together. Adhesive has also been used to bond discrete pieces, such as the fasteners and leg elastics, to the article. Typically, the adhesive has been sprayed or slot-coated on the continuous moving web which provides the absorbent articles. The sufficiency of the adhesive bond between the components of the absorbent article is generally dependent upon the amount of adhesive, the type of adhesive and the pattern of the adhesive.

Various techniques for spraying an adhesive on a moving web are well known to those skilled in the art. Many conventional techniques have relied upon pressure to deliver the adhesive to a plurality of nozzles and spray the adhesive from the nozzles onto a moving web. In such conventional techniques, the amount and pattern of the spray of adhesive is directly dependent upon the pressure at each nozzle.

For example, one conventional technique which relies upon pressure for spraying the adhesive involves an apparatus having a plurality of nozzles which are connected to a manifold. Adhesive is supplied to the manifold and nozzles by a single large, central tank of molten adhesive. The tank of adhesive is pressurized to deliver the adhesive from the tank to the manifold and to the individual nozzles. The individual nozzles are then independently turned on and off to spray the adhesive. The amount of adhesive which is dispensed from the nozzles is dependent upon the pressure at the tank of adhesive, the length of the supply lines, the number of nozzles which are being operated at a given point in time and whether the nozzles are operating efficiently.

Various problems, however, exist is spraying an adhesive on a moving web. For instance, it is very difficult to control the placement of the adhesive on the web and to control the amount of adhesive applied to the web. Collateral spray of adhesive, for instance, can land on portions of the moving web where adhesive is not desired and/or on the processing equipment. In addition, some spray adhesives lack adhesive strength, especially when applying elastic components to a web that are later to be stretched.

In addition to spraying adhesives onto a moving web, hot melt adhesives are also applied by being extruded onto a web using a slot coater or similar device. In these processes, the moving web contacts the adhesive head and the adhesive is periodically applied to the web. At faster web speeds, however, the application of a hot melt adhesive through extrusion can be the rate limiting step in the process. For instance, due to the speed of the web, even short pulses of adhesive form relatively long lengths of adhesive streaks. For instance, during conventional processes, the moving web is in constant contact with the adhesive head. A single bead of adhesive extruded from the adhesive head contacts the moving web and is smeared over the web as the web is moving past the adhesive head. These adhesive streaks typically must be covered by a material joined to the web. Thus, long adhesive streaks require longer pieces of material, which may represent excess material and waste in the final product. In order to create shorter streaks of adhesive, the process speeds, i.e. the speed of the moving web, must be decreased. Consequently, the adhesive application step of the process can be a rate limiting step and can adversely affect the overall throughput of the process.

In addition to problems experienced in applying adhesives at fast speeds, adhesive applicators as described above also have experienced problems with maintaining uniform flow through the adhesive head due to clogging and other issues. For instance, over time, adhesive heads can generate significant amounts of dust and lint. In addition, adhesive build up on the head can occur over time. Thus, adhesive applicators are typically periodically cleaned which can require downtime of the process.

In view of the above, a need exists for an improved method and system for applying an adhesive, such as a hot melt adhesive, to a moving web. More particularly, a need exists for an adhesive applicator system and method capable of controlling the amount of adhesive being applied to a web while the web is moving at very fast speeds that results in an adhesive pattern applied to the web that provides advantages and benefits in producing a product.

SUMMARY

In general, the present disclosure is directed to a system and process for applying an adhesive to a moving web of material in order to form a distinct and unique adhesive pattern on the moving web. The adhesive pattern can include various characteristics that not only minimize material usage to build products but can also result in various advantageous bonding regimes.

In one embodiment, for instance, the present disclosure is directed to a material having an adhesive pattern for incorporating the material into a product. The material includes a base web having a first surface and a second and opposite surface. In accordance with the present disclosure, a pattern of treated discrete areas reside on the first surface of the base web. The treated discrete areas are formed from an adhesive composition. The treated discrete areas are generally parallel to each other and have a length extending in the length direction of the base web. Each treated discrete area includes a head portion and a tail portion. In one embodiment, the ratio of the length of the head portion to the length of the tail portion is from about 1:2 to about 1:50, such as from about 1:5 to about 1:40. The pattern of treated discrete areas can include from about 2 to about 30 treated discrete areas, such as from about 3 to about 12 treated discrete areas. The length of each treated discrete area can be relatively small even when applied to the web at very fast speeds. For instance, the length of each treated discrete area can be less than about 80 mm, such as less than about 45 mm, such as less than about 20 mm.

In one embodiment, the adhesive composition can have a basis weight in the head portion that is greater than a basis weight of the adhesive composition in the tail portion. For example, the basis weight of the adhesive composition in the head portion can be at least 50% greater than the basis weight of the adhesive composition in the tail portion.

For example, in one embodiment, the adhesive composition contained in the head portion when measured in grams per linear meter can be greater than the amount of adhesive composition contained in the tail portion when measured in grams per linear meter. For instance, the adhesive composition in grams per linear meter in the head portion can be at least about 20% greater, such as at least about 50% greater, such as at least about 100% greater than the amount of adhesive composition contained in the tail portion in grams per linear meter. For example, the ratio of the adhesive composition contained in the head portion in grams per linear meter in comparison to the amount of adhesive composition contained in the tail portion in grams per linear meter can be from about 1.5:1 to about 50:1.

In one embodiment, for instance, the weight ratio of the amount of adhesive composition contained in each head portion in comparison to the amount of adhesive composition contained in each tail portion can be from about 95:5 to about 5:95. In one embodiment, more of the adhesive composition can be contained in the head portion. For example, the weight ratio of the amount of adhesive composition contained in each head portion in comparison to the amount of adhesive composition contained in each tail portion can be from about 90:10 to about 60:40.

The head portion can generally be wider than each corresponding tail portion. For example, the head portion of each treated discrete area can have a width and wherein the maximum width of the head portion can be larger than the maximum width of the tail portion. The head portion, for instance, can have a circle-like or oval-like shape and can taper inwardly when joining with the tail portion. The tail portion, in one embodiment, can have a substantially uniform width.

The treated discrete areas can be applied to the web of material at any suitable location. In one embodiment, the treated discrete areas can extend in the machine direction of the web of material or length direction. The tail portion of each treated discrete area can be positioned downstream from the head portion of each treated discrete area.

The adhesive composition can comprise a thermoplastic polymer, such as an elastomeric polymer. The thermoplastic polymer, for instance, may comprise a polyolefin polymer, a styrene block copolymer, or mixtures thereof. The adhesive composition may also contain a tackifier, a plasticizer, and/or various other additives. In one embodiment, the adhesive composition comprises a hot melt adhesive. The adhesive composition, for instance, can have a viscosity of from about 500 cps to about 20,000 cps when measured at a temperature of 350° F.

The tail portion of each treated discrete area can include a middle section and an end section. The end section can be located opposite the head portion. The middle section can have a substantially uniform basis weight while the end section can have a gradually decreasing basis weight.

The base web can comprise any suitable material. For instance, the base web may comprise a nonwoven web, a woven web, a knitted web, a paper web, a tissue web, or a film. In one embodiment, the base web comprises a spunbond web, a meltblown web, a conform web, a hydroentangled web, a tissue web, or laminates thereof. For instance, in one particular embodiment, the base web comprises a laminate containing a meltblown web sandwiched inbetween a first spunbond web and a second spunbond web. The material treated in accordance with the present disclosure can be incorporated into an absorbent article. The absorbent article, for instance, may comprise a diaper.

Other features and aspects of the present disclosure are discussed in greater detail below.

BRIEF DESCRIPTION OF DRAWINGS

A full and enabling disclosure of the present disclosure is set forth more particularly in the remainder of the specification, including reference to the accompanying figures, in which.

Repeat use of reference characters in the present specification and drawings is intended to represent the same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a system and method for accurately applying an adhesive onto a continuously moving web in a desired pattern. The apparatus and method are particularly useful for applying viscous adhesives, such as hot melt adhesives, to bond together different components of various different products, such as a disposable absorbent article. The system and method of the present disclosure, for instance, can be used to bond elastic panels, side panels, fastener panels, leg elastics, and the like to other materials during the production of an absorbent article, such as a diaper, an adult incontinence product, a training pant, a swim pant, a feminine hygiene product, or the like. It should be understood, however, that the system and process can also be used in numerous and various other applications and is not in any way limited to the production of absorbent articles.

The system of the present disclosure generally includes a web conveying device that conveys the web adjacent to an adhesive applicator. The system further includes a web deflecting device that periodically causes the moving web to contact a nozzle of the adhesive applicator. Adhesive, in one embodiment, intermittently exits the nozzle of the adhesive applicator for application to the web. The adhesive can flow from the nozzle prior to contact with the web. In this manner, during contact with the web, the adhesive is smeared onto the web in a controlled manner. The system and process of the present disclosure provide numerous benefits and advantages in processing webs of material. For instance, the amount of adhesive and the length of adhesive that extends in the machine direction (i.e. moving direction or longitudinal direction) can be minimized at extremely fast web speeds. In addition, controlling the timing of supply of adhesive to the nozzle allows for extremely accurate control over the desired amount of adhesive to be applied to the web.

In this manner, less materials are needed in constructing the product, such as the absorbent article. In addition, line speeds can be increased in comparison to the use of conventional adhesive applicators.

Due to the manner in which the adhesive composition is applied to the moving web, various unique and distinctive adhesive patterns can be formed on the web that provide various advantages and benefits. The adhesive pattern, for instance, may comprise a plurality of treated discrete areas that extend in the longitudinal direction of the web. Each treated discrete area can have a distinctive head portion integral with a tail portion. The treated discrete areas can have an adhesive composition distribution that facilitates bonding to other materials and can also facilitate processing. The treated discrete areas, for instance, can have relatively short lengths even when applied to the web at very high speeds.

Figure 1:
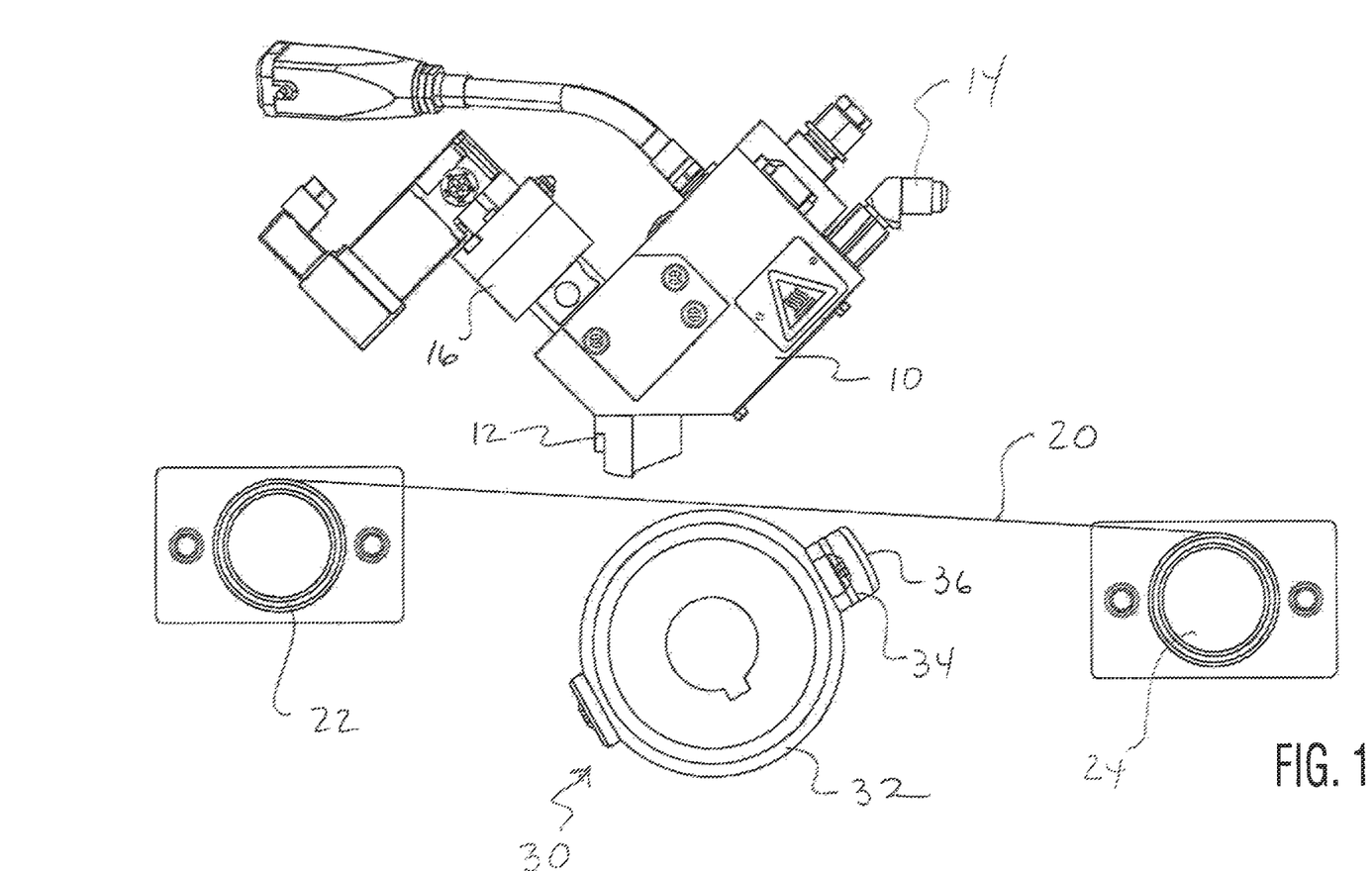
FIG. 1 is a side view of one embodiment of a system for applying an adhesive to a moving web of material illustrating an adhesive applicator in relation to a web deflecting device.
Figure 2:
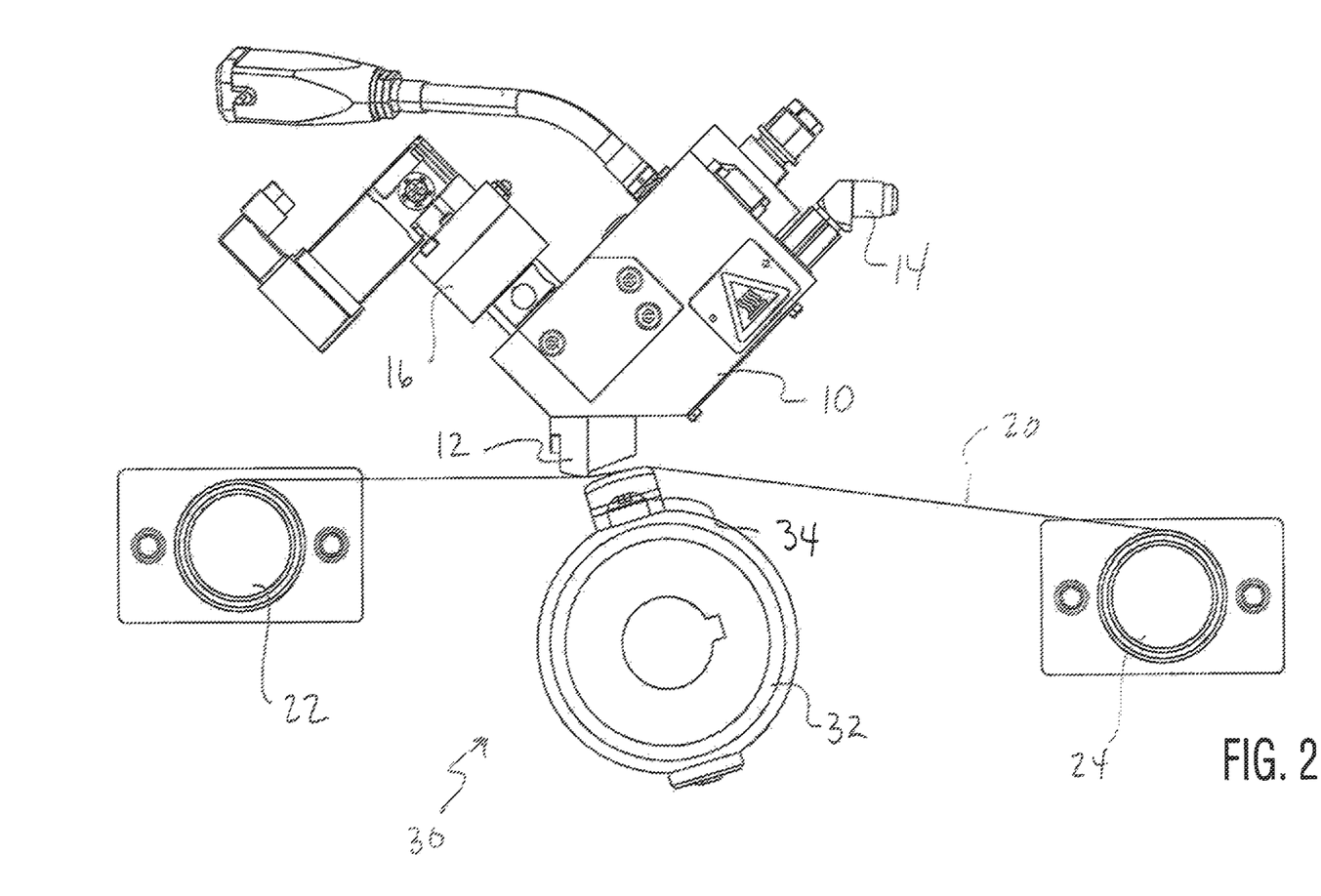
FIG. 2 is a side view of the system illustrated in FIG. 1 showing the web deflecting device deflecting a web of material into contact with an adhesive nozzle.
Figure 3:
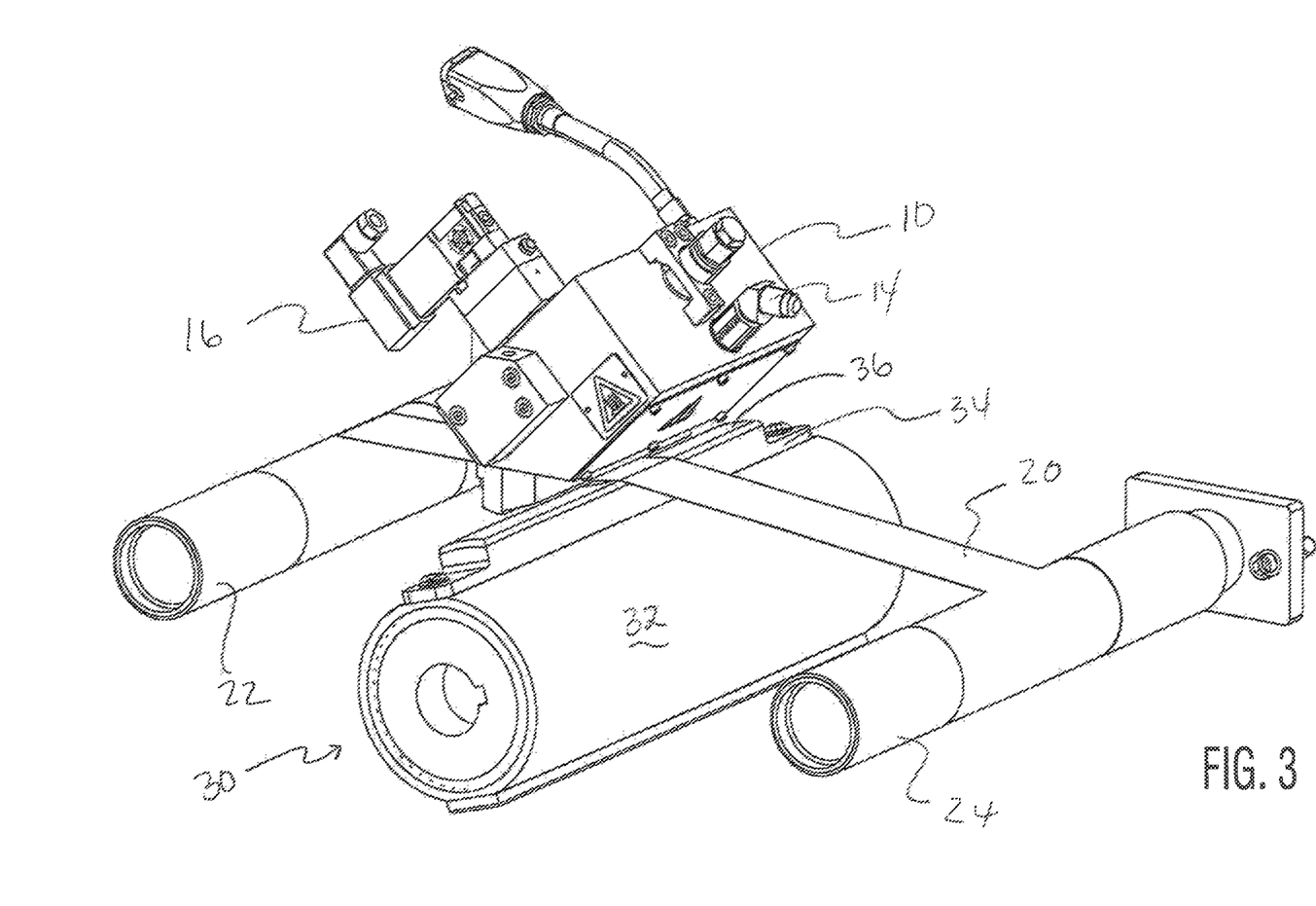
FIG. 3 is a perspective view of the system for applying an adhesive to a moving web as shown in FIGS. 1 and 2.

Referring to FIGS. 1 through 3, one embodiment of an adhesive applicator system made in accordance with the present disclosure is illustrated. As shown, the system includes an adhesive applicator 10 that includes a nozzle 12. The nozzle 12, for instance, may comprise a slot coating device. In one embodiment, the nozzle 12 can include a single adhesive orifice or slot. The orifice may be designed to apply adhesive to a particular location on a web of material or can be designed to apply adhesive over the entire width of the material.

Alternatively, the nozzle 12 may include a plurality of spaced apart exit ports or slots for depositing a plurality of parallel treated discrete areas of adhesive onto a moving web. The nozzle 12 can receive adhesive from an adhesive supply. For instance, as shown in the figures, the adhesive applicator 10 can include an adhesive supply line 14 in fluid communication with the nozzle 12.

The adhesive applicator 10 further includes an adhesive flow control device 16. The adhesive flow control device 16 controls the flow of adhesive from the supply line 14 to the one or more exit ports on the nozzle 12. The flow control device 16 can comprise, for instance, any suitable valve or similar device. In one embodiment, for instance, the adhesive flow control device 16 may comprise a solenoid valve. In one embodiment, the adhesive flow control device 16 can be in communication with a controller, such as one or more microprocessors. The controller can be configured to control the adhesive flow control device 16 for enabling and disabling flow of an adhesive through the nozzle 12 at desired times, such as during periodic intervals. For example, the adhesive flow control device 16 may open the valve to allow the adhesive to flow through the nozzle 12 and may close the valve to cease the flow of adhesive through the nozzle 12.

The adhesive applicator 10 can include a single adhesive control device 16 or can include multiple devices. Additionally, the adhesive applicator 10 can include a single valve or multiple valves. For instance, if the nozzle 12 includes a plurality of exit ports, the adhesive applicator 10 can include a corresponding plurality of control devices 16 and/or valves for controlling each of the individual exit ports. Alternatively, a single control device 16, along with either a single valve or multiple valves, can control flow through all of the exit ports simultaneously.

The system of the present disclosure further includes a web conveying device for conveying a web of material. As shown in FIGS. 1 through 3, the web conveying device can include guide rolls 22 and 24 for supporting a web of material 20. As shown in FIG. 1, the guide rolls 22 and 24 are positioned to convey the web of material 20 in close proximity to the nozzle 12 without contacting the nozzle.

The web conveying device can be designed to convey the web 20 at very fast speeds. For instance, the web 20 during processing can be moving at a speed of at least about 100 m/min, such as at least about 200 m/min, such as at least about 300 m/min, such as at least about 400 m/min, such as at least about 450 m/min, such as at least about 500 m/min, such as at least about 550 m/min, such as at least about 600 m/min. The speed of the web of material 20 is generally less than about 1,000 m/min, such as less than about 800 m/min.

In accordance with the present disclosure, the system further includes a web deflecting device 30 that is designed to periodically cause contact between the nozzle 12 and the web of material 20. In the embodiment illustrated in FIGS. 1 through 3, the web deflecting device contacts the web 20 moving the web into contact with the nozzle 12. In other embodiments, however, the web deflecting device may move the nozzle into contact with the web. In general, the web deflecting device can be any suitable device or apparatus capable of causing contact between the nozzle 12 and the moving web of material 20.

In the embodiment illustrated in FIGS. 1 through 3, the web deflecting device includes a rotating roll 32 attached to a deflecting cam 34. The deflecting cam 34 extends radially outward from the roll 32 and includes a web contacting surface 36. The web contacting surface 36 can have a width that can correspond with the width of the moving web 20. In general, the width of the web contacting surface 36 is at least as wide as the one or more exit ports located on the nozzle 12.

In order to apply adhesive from the nozzle 12 of the adhesive applicator 10 to the moving web 20, the web deflecting device 30 is rotated, which causes the web contacting surface 36 of the deflecting cam 34 to contact the web 20 as shown in FIGS. 2 and 3. For at least a portion of the rotation of the web deflecting device 30 where the deflecting cam 34 is in contact with the web 20, the web 20 comes into contact with the nozzle 12. During contact between the web of material 20 and the nozzle 12, adhesive is transferred to the web. The web deflecting device 30 continues to rotate causing the deflecting cam 34 to rotate out of the path of travel of the web of material 20 causing the web to once again move away from the nozzle 12 and to continue to move downstream in a non-contacting relationship with the adhesive applicator 10.

In order to apply adhesive to the web of material 20, the adhesive control device 16 can be used to control the flow of adhesive from the nozzle 12 in a manner that forms the desired pattern of adhesive onto the web. For example, enabling flow of adhesive and disabling flow of adhesive from the nozzle in conjunction with the timing of contact between the nozzle and the moving web can be varied and adjusted in order to obtain an optimum result for the particular application.

In one embodiment, for instance, flow of adhesive through the nozzle 12 is started and stopped prior to any contact of the nozzle 12 with the web 20. For example, the flow control device 16 may cause the one or more valves to open for a period of time, allowing adhesive to flow to the nozzle 12, and then close the one or more valves, causing the adhesive to cease flowing to the nozzle 12, all during a time period where the web 20 is not in contact with the nozzle 12. In this embodiment, for instance, a bead of adhesive is discharged from the exit port of the nozzle 12. Due to the fluid properties of the adhesive, the adhesive remains adhered to the nozzle head. The web of material 20 is then brought into contact with the bottom surface of the nozzle 12 by the web deflecting device 30. The bead of adhesive is then removed from the surface of the nozzle 12 due to contact with the moving web. Due to the manner in which the adhesive is wiped off the nozzle 12, a streak of adhesive is then deposited onto the web 20 in the longitudinal direction or the machine direction of the moving web.

In an alternative embodiment, flow of adhesive through the nozzle 12 is enabled by the adhesive control device 16 prior to contact with the moving web. For example, the flow control device 16 may cause the one or more valves to open allowing adhesive to flow to the nozzle 12. In this embodiment, however, the one or more valves remain open as the web 20 contacts the nozzle 12. Accordingly, flow of adhesive through the nozzle 12 continues for at least a portion of the time period during which the nozzle 12 is in contact with the web 20. The adhesive control device 16 can disable flow of adhesive at any point during contact with the web 20, for instance by closing the one or more valves. For example, flow of adhesive can be discontinued just as the web 20 contacts the nozzle 12 for applying lesser amounts of adhesive or can discontinue the flow of adhesive generally at the same time the web 20 separates from the nozzle 12 for applying greater amounts of adhesive. In still further embodiments, the flow of adhesive may be stopped after contact between the web 20 and the nozzle 12 has ceased.

Thus, the system and process of the present disclosure provides a significant amount of variability in the amount of adhesive that is applied to the web depending upon the application. The length of adhesive in the longitudinal direction can be controlled by controlling the amount of adhesive that flows through the nozzle 12, the duration of flow of adhesive, and/or the timing of the flow of adhesive in relation to contact with the moving web.

In accordance with the present disclosure, the amount of time that the web 20 contacts the surface of the nozzle 12 can also be controlled depending upon various factors. The amount of time the web 20 remains in contact with the nozzle 12, for instance, depends upon the speed of the web and the construction of the web deflecting device 30, including the shape of the deflecting cam 34. The contact time, for instance, can depend upon the amount the web 20 is deflected towards the adhesive applicator 10 and can also depend upon the length of the web contacting surface 36 in the longitudinal direction. In one embodiment, for instance, the system of the present disclosure can be configured such that the web of material 20 contacts the nozzle 12 for at least about 4 milliseconds, such as at least about 6 milliseconds, such as at least about 8 milliseconds, such as at least about 10 milliseconds, such as at least about 12 milliseconds. The contact time is generally less than about 1 second, such as less than about 500 milliseconds, such as less than about 200 milliseconds, such as less than about 100 milliseconds, such as less than about 50 milliseconds, such as less than about 40 milliseconds, such as less than about 30 milliseconds, such as less than about 20 milliseconds, such as less than about 15 milliseconds.

During the process, the adhesive is deposited onto the moving web of material 20 so as to form treated discrete areas on the web. For instance, when the nozzle 12 includes a plurality of spaced apart exit ports, a pattern of treated discrete areas can be formed on one surface of the moving web 20. The treated discrete areas are generally parallel to each other and extend in a longitudinal direction or the machine direction of the web 20. Due to the speed of the moving web and continuous contact between the web and the adhesive nozzle, conventional adhesive applicators tended to apply relatively long streaks of adhesive to the web and provided little to no control over the adhesive pattern. The system of the present disclosure, however can apply relatively short streaks of adhesive to a web of material 20 moving at very rapid speeds. For example, for a web of material 20 moving at a speed of greater than about 100 m/min, such as greater than about 300 m/min, such as even greater than about 600 m/min, the streaks of adhesive can have a length in the longitudinal direction of generally less than about 80 mm, such as less than about 60 mm, such as less than about 50 mm, such as less than about 45 mm, such as less than about 40 mm, such as less than about 30 mm, such as less than about 25 mm, such as less than about 20 mm, such as less than about 15 mm, such as less than about 13 mm, such as less than about 10 mm, such as less than about 8 mm, such as even less than about 5 mm. The adhesive lengths are generally greater than about 2 mm, such as greater than about 4 mm, such as greater than about 5 mm.

In addition to being capable of controlling the amount of adhesive applied to the moving web 20 and being able to reduce the adhesive application length when running at high speeds, the process and system of the present disclosure also provides for a self-cleaning mechanism of the nozzle. For example, by periodically contacting the nozzle 12 as shown is FIGS. 1 through 3, the web of material 20 wipes the surface of the nozzle 12 clean during application of the adhesive to the web 20. Thus, during application of the adhesive to the moving web 20, the web 20 wipes away the adhesive residing on the nozzle 12 and simultaneously wipes away any lint on the nozzle head.

In one embodiment the deflecting cam 34 of the web deflecting device 30 contacts the moving web 20 and pushes the web above the exit ports on the nozzle 12. In this manner, the web 20 forms an exit angle with the nozzle 12.

Figure 4:
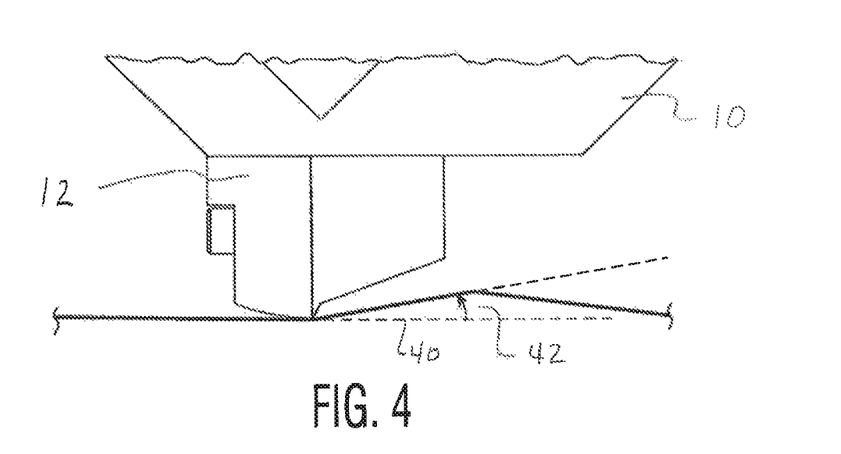
FIG. 4 is a side view of a nozzle for an adhesive applicator illustrating an exit angle.

Referring to FIG. 4, for instance, the exit ports on the nozzle 12 are perpendicular to a horizontal plane 40. When the web of material 20 is deflected, the web of material 20 forms an exit angle 42 in relation to the horizontal plane 40. During contact with the nozzle 12, the exit angle 42 of the web of material 20 with the exit ports on the nozzle changes from a minimum exit angle to a maximum exit angle. The maximum exit angle during the process, for instance, can generally be greater than about 5°, such as greater than about 7°, such as greater than about 10°, such as greater than about 12°, such as greater than about 15°, such as greater than about 18°, such as greater than about 20°, such as greater than about 22°, such as greater than about 25°. The maximum exit angle is generally less than about 50°, such as less than about 30°, such as less than about 25°, such as less than about 20°. As the exit angle 42 of the web of material 20 changes with respect to the nozzle 12, the wiping motion of the web 20 against the nozzle 12 changes further facilitating cleaning of the nozzle 12 during the process. Changing the exit angle 42 during the process also facilitates application of adhesive to the web 20 and provides greater uniformity and control.

In addition to forming and changing the exit angle of the web 20 with the nozzle 12, the tension of the web 20 as it contacts the nozzle 12 can also be varied in order to facilitate application of the adhesive to the web 20 and/or further clean the surface of the nozzle 12 during contact. For example, in one embodiment, the rotating roll 32 of the web deflecting device 30 can be rotated so that the web contacting surface 36 of the deflecting cam 34 contacts the web 20 at a speed that is faster than the speed the web 20 is moving. In this manner, tension in the web 20 can be increased during contact with the nozzle 12. For example, the web contacting surface 36 can be moving at a speed that is at least about 1% greater, such as at least about 2% greater, such as at least about 3% greater, such as at least about 4% greater, such as at least about 5% greater than the speed at which the web 20 is moving during contact with the web 20. The speed of the web contacting surface 36 is generally moving at a speed that is no more than about 30% greater than the speed of the web 20, such as no more than about 20% greater than the speed of the web 20, such as no more than about 10% greater than the speed of the web 20.

In the embodiment illustrated in FIGS. 1 through 3, the web deflecting device 30 is positioned in the system such that the web contacting surface 36 contacts the web 20 downstream from the nozzle 12. For instance, the web contacting surface 36 can contact the web of material 20 a distance downstream from the one or more exit ports from the nozzle 12 a distance of greater than about 20 mm, such as greater than about 40 mm, such as greater than about 60 mm, such as greater than about 80 mm, such as greater than about 100 mm. The distance downstream can generally be less than about 1000 mm, such as less than about 500 mm, such as less than about 100 mm.

In an alternative embodiment, instead of contacting the web 20 downstream from the nozzle 12, the web deflecting device 30 can also be positioned to contact the web 20 upstream from the nozzle 12. When contacting the web 20 upstream from the nozzle 12, an entrance angle will be formed between the web 20 and a horizontal plane that is perpendicular to the exit port on the nozzle 12. The entrance angle can have the same dimensions as the exit angle 42 described above.

It should also be understood that the web deflecting device 30 as shown in FIGS. 1 through 3 represents one embodiment of the web deflecting device 30 and that various other web deflecting devices may be utilized. For instance, in an alternative embodiment, the web deflecting device 30 may be configured to move the deflecting cam 34 up and down instead of in a rotating motion.

The adhesive that is emitted or extruded from the nozzle 12 in accordance with the present disclosure can vary depending upon various factors including the type of material 20 being processed, the type of product being formed, and the type of opposing material that is later attached to the web of material 20. In one embodiment, for instance, the adhesive applied to the web 20 may comprise a hot melt adhesive, such as a hot melt, pressure-sensitive adhesive. For example, in one embodiment, an adhesive composition is applied to the web of material 20 containing a thermoplastic polymer which may comprise an elastomeric polymer. The polymer may be combined with one or more tackifying resins and/or one or more plasticizers. Optionally, the adhesive composition may also contain an oil, a wax, and/or a stabilizer.

In one embodiment, the polymer contained in the adhesive composition is a polyolefin polymer. The polyolefin polymer may comprise a polypropylene, a polyethylene, copolymers thereof, homopolymers thereof, and the like. In an alternative embodiment, the polymer contained in the polymer composition contains a block copolymer, such as a styrene block copolymer. The block copolymer, for instance, may comprise, a polystyrene-polybutadiene-polystyrene polymer, a polystyrene-polyisoprene-polystyrene polymer, a polystyrene-polyisoprene-polybutadiene-polystyrene polymer, a polystyrene-poly(ethylenebutylene)-polystyrene polymer, a polystyrene-poly(ethylenepropylene)-polystyrene polymer, or mixtures thereof. One or more of the block copolymers can also be combined with a polyolefin as described above.

In general, the adhesive composition can contain one or more polymers in an amount greater than about 25% by weight, such as in an amount greater than about 30% by weight, such as in an amount greater than about 35% by weight, such as in an amount greater than about 40% by weight, such as in an amount greater than about 50% by weight, such as in an amount greater than about 60% by weight, such as in an amount greater than about 70% by weight. One or more polymers may be contained in the adhesive composition in an amount less than about 98% by weight, such as in an amount less than about 80% by weight, such as in an amount less than about 70% by weight, such as in an amount less than about 60% by weight, such as in an amount less than about 50% by weight.

Tackifying resins that may be combined with the polymer include, for instance, colophony rosins, terpene resins, copolymers based on natural terpenes, or resins that have been hydrogenated, polymerized or copolymerized with an aromatic hydrocarbon.

The use of a tackifying resin in an adhesive composition is optional. When present the tackifying resin can be included in the composition generally in an amount greater than about 10% by weight, such as in an amount greater than about 20% by weight, such as in an amount greater than about 30% by weight. Tackifying resins are generally present in an amount less than about 70% by weight, such as in an amount less than about 60% by weight, such as in an amount less than about 50% by weight.

Use of plasticizers in the adhesive composition is also optional. When present, a plasticizer can be included in the composition in an amount greater than about 5% by weight, such as in an amount greater than about 10% by weight, such as in an amount greater than about 15% by weight, and generally less than about 30% by weight, such as in an amount less than about 25% by weight, such as in an amount less than about 20% by weight. Suitable plasticizers that may be included in the adhesive composition include mineral oil, vegetable oils, animal oils, and derivatives thereof. Petroleum derived oils may also be used as plasticizers.

As described above, beginning a flow of the adhesive composition through the nozzle 12 can occur prior to contact of the nozzle 12 with the moving web 20. Thus, the adhesive composition used in the present disclosure, in one embodiment, has sufficient cohesive properties such that the adhesive will not drip from the surface of the novel during flow. For example, in one embodiment, the adhesive composition has sufficient viscosity and cohesiveness to remain adhered to the surface of the nozzle 12 until contact with the moving web 20.

For instance, the adhesive composition can have a viscosity at 350° F. (176° C.) of generally greater than about 500 cps, such as greater than about 600 cps, such as greater than about 700 cps, such as greater than about 800 cps, such as greater than about 900 cps, such as greater than about 1000 cps, such as greater than about 1200 cps, such as greater than about 1400 cps, such as greater than about 1600 cps, such as greater than about 1800 cps, such as greater than about 2000 cps, such as greater than about 2200 cps, such as greater than about 2500 cps, such as greater than about 2700 cps, such as greater than about 3000 cps, such as greater than about 3500 cps, such as greater than about 4000 cps. The viscosity of the adhesive composition is generally less than about 90,000 cps at 350° F., such as less than about 80,000 cps, such as less than about 70,000 cps, such as less than about 60,000 cps, such as less than about 50,000 cps, such as less than about 40,000 cps, such as less than about 30,000 cps, such as less than about 20,000 cps, such as less than about 10,000 cps, such as less than about 8000 cps, such as less than about 5000 cps, such as less than about 3000 cps.

The Viscosity Test is conducted in accordance with ASTM Test Method D3236-88, entitled "Standard Test Method for Apparent Viscosity of Hot Melt Adhesives and Coating Materials," the entire disclosure of which is incorporated herein by reference, with the following parameters. The viscometer used is that made by Brookfield Engineering Laboratories of Middleboro, Mass., U.S.A., as model RVDV III. The spindle number to use in conducting the ASTM Test Method is SC4-27. The sample size should be about 10.5 grams of adhesive. The spindle speed (rpm) is set to a value that results in a torque reading in the range of 20 percent to 80 percent. A reading should be taken every few minutes for about 15 minutes, or until the viscosity values stabilize, after which the final viscosity reading (in centipoises) is recorded.

The system and process of the present disclosure is capable of producing a unique adhesive pattern applied to the moving web 20. For instance, through the process of the present disclosure, an adhesive pattern of treated discrete areas can be formed onto the moving web 20. These treated discrete areas can have many beneficial properties for attaching the moving web 20 to an adjoining surface, such as to another piece of material. For example, in one embodiment, the adhesive pattern made according to the present disclosure can be applied to the web 20 at high speeds while minimizing the amount of materials needed to construct a product. In addition, the adhesive pattern may include treated discrete areas having a unique adhesive profile that facilitates attachment to another material and provides for a strong bond.

For example, in one embodiment, the nozzle 12 of the adhesive applicator 10 includes a plurality of exit ports. For instance, the nozzle 12 can include greater than about 2 exit ports, such as greater than about 4 exit ports, such as greater than about 6 exit ports, such as greater than about 8 exit ports, such as greater than about 10 exit ports and generally less than about 30 exit ports, such as less than about 20 exit ports, such as less than about 15 exit ports that extend along the width of the web of material 20. The plurality of exit ports can be used to form a pattern of treated discrete areas on the top surface of the moving web 20. The treated discrete areas form streaks on the surface of the web 20 and generally extend in the longitudinal direction of the web 20 or the machine direction.

Figure 5:
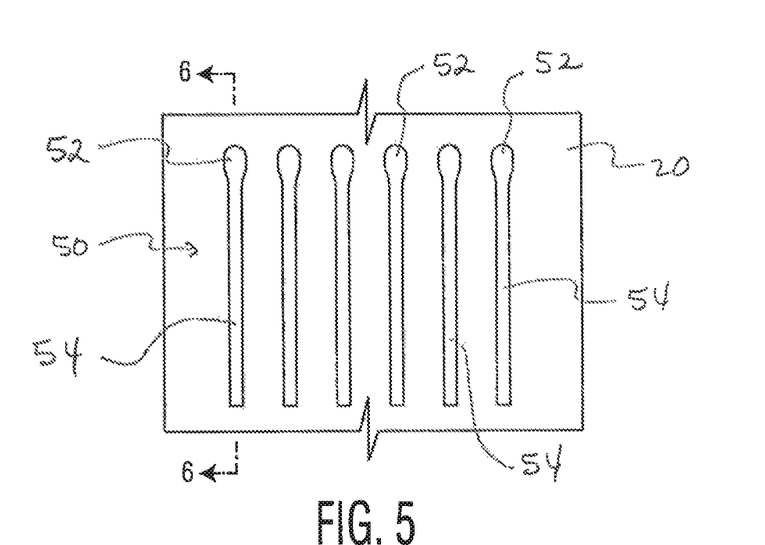
FIG. 5 is a plan view of a web of material illustrating an adhesive pattern applied to the material.
Figure 6:
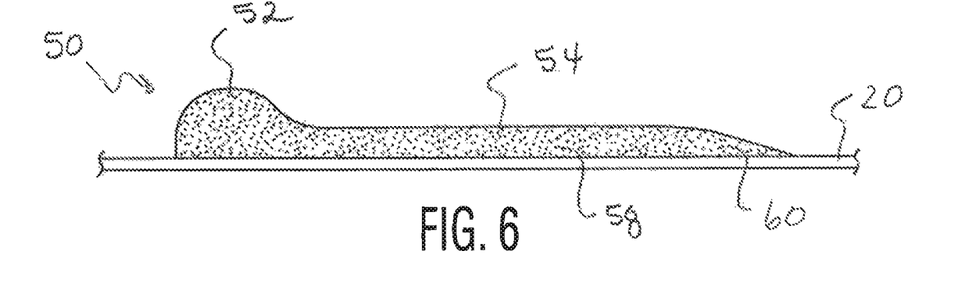
FIG. 6 is a cross sectional view of the woven material illustrated in FIG. 5.

For instance, one example of a pattern of treated discrete areas of an adhesive composition is shown in FIGS. 5 and 6. Referring to FIG. 5, for example, a plurality of vertically extending treated discrete areas 50 are shown applied to the web 20. The treated discrete areas 50 are generally parallel to each other in the length direction of the web 20. In FIG. 5, six parallel discrete areas are shown. It should be understood, however, that a greater number or lesser number of treated discrete areas may be formed on the web 20. For example, in one embodiment, from about 2 to about 30 treated discrete areas, such as from about 3 to about 12 treated discrete areas can be formed on the web of material 20.

As shown in FIG. 5, in one embodiment, each treated discrete area can include a head portion 52 integral with a tail portion 54. The head portion 52 is formed when the web of material 20 first contacts the nozzle 12 during the process. The tail 54, on the other hand, is formed as the web of material 20 moves across the head of the nozzle 12. A cross section of one of the treated discrete areas 50 showing the head portion 52 and the tail portion 54 is illustrated in FIG. 6.

Figure 7:
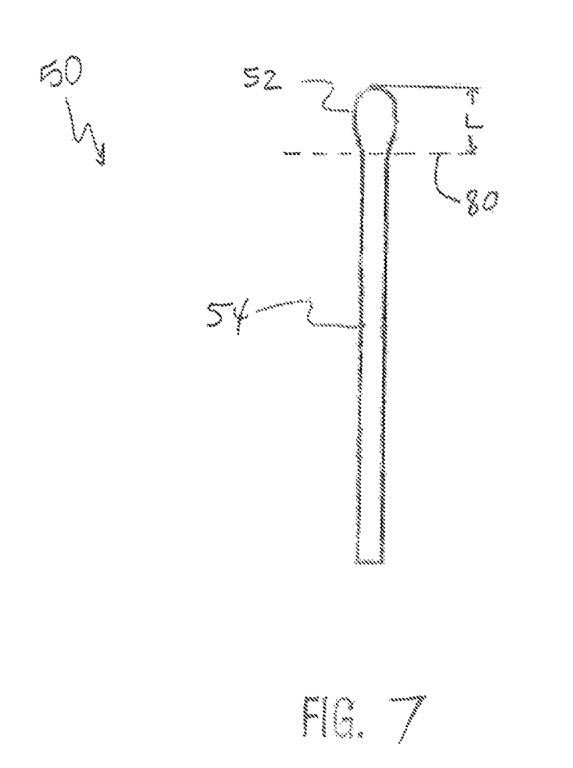
FIG. 7 is a plan view of an enlarged view of one of the adhesive streaks shown in FIG. 5.

Referring to FIG. 7, one of the treated discrete areas 50 is shown in greater detail. The treated discrete area 50 includes a head portion 52 and a tail portion 54. In FIG. 7, a broken line 80 is used to illustrate where the head portion 52 ends and the tail portion 54 begins. For most applications, the head portion 52 is visually distinct from the tail portion 54. For example, in one embodiment, the head portion 52 will appear more as a bead or glob of adhesive composition, while the tail portion 54 appears more like a smear or streak of the adhesive composition. As shown in FIG. 7, the tail portion 54 typically has a more uniform width than the head portion 52. The width of the tail portion 54 generally corresponds to the width of the exit orifice on the nozzle 12. As used herein, the head portion is defined as the area above the tail portion wherein the tail portion is the part of the treated discrete area 50 where a relatively uniform width is achieved as shown in FIG. 7. The head portion, on the other hand, can have various irregular shapes and can generally have a width that is wider than the width of the tail portion 54. As shown in FIG. 7, the position of the line of demarcation 80 is where the head portion 52 tapers inward and joins the tail portion 54.

As shown in FIG. 5, in one embodiment, the head portion 52 can have a maximum width that is wider than the maximum width of the corresponding tail portion 54. The tail portion 54, on the other hand, can be substantially longer than a corresponding head portion 52. For example, the ratio of the length of the head portion 52 to the length of the tail portion 54 is generally greater than about 1:5, such as greater than about 1:10, such as greater than about 1:15, such as greater than about 1:20. The ratio of the length of the head portion 52 to the length of the tail portion 54 is generally less than about 1:100, such as less than about 1:40, such as less than about 1:30, such as less than about 1:20. As described above, the length of the treated discrete area 50 can vary depending upon the particular application but can be less than about 80 mm, such as less than about 70 mm, such as less than about 60 mm, such as less than about 50 mm, such as less than about 45 mm, such as less than about 40 mm, such as less than about 35 mm, such as less than about 30 mm, such as less than about 25 mm, such as less than about 20 mm, such as even less than about 15 mm. These short lengths can be achieved even when the web of material 20 is being conveyed at extremely fast speeds, such as greater than about 400 m/min.

The amount of adhesive composition contained in each head portion 52 in relation to the amount of adhesive composition contained in a corresponding tail portion 54 can vary by controlling the web speed, the web deflecting device 30 and the adhesive flow rates. For instance, in general, the amount of adhesive composition contained in each head portion 52 in comparison to the amount of adhesive composition contained in each tail portion 54 can be from about 95:5 to about 5:95. In one embodiment, however, a greater amount of adhesive composition may be contained in head portion 52 in relation to the amount of adhesive composition as contained in the tail portion 54. For example, a bead of the adhesive composition first contacts the web of material 20 during the process forming the head portion 52 followed by formation of the tail portion 54 through a smearing process. In these embodiments, for instance, the amount of adhesive composition contained in each head portion 52 in comparison to the amount of adhesive composition contained in each tail portion 54 can be from about 90:10 to about 60:40.

As shown in FIG. 6, for instance, the adhesive composition can have a basis weight (i.e. amount of adhesive composition per area on the web) in the head portion 52 that is greater than the basis weight of the adhesive composition in the tail portion 54. For example, the basis weight of the adhesive composition in the head portion 52 can be at least about 20%, such as at least about 30%, such as at least about 40%, such as least about 50%, such as least about 60%, such as least about 70%, such as least about 80%, such as least about 90%, such as even at least about 100% greater than the basis weight of the adhesive composition in the tail portion 54.

As used herein, the basis weight of the adhesive composition refers to an average basis weight over the particular area taken up by the adhesive composition on the web 20. For instance, the basis weight of the adhesive composition in the head portion 52 would be the average basis weight of the adhesive composition over the area occupied by the head portion 52. Similarly, the basis weight of the adhesive composition in the tail portion 54 would be the average basis weight of the adhesive composition over the area occupied by the tail portion 54.

In one embodiment, the amount of adhesive in the head portion 52 and the amount of adhesive in the tail portion 54 can be measured on a grams per linear meter basis. When measuring the amount of adhesive composition in the different portions based on a grams per linear meter basis, the total weight of the adhesive composition in grams in a particular portion can be divided by the length of the particular portion in the machine direction or in the length direction. For instance, as shown in FIG. 7, the amount of adhesive composition in the head portion 52 can first be measured. In one embodiment, for instance, the head portion 52 can be removed from the web of material 20 and weighed in grams. An untreated portion of the web material can also be weighed having the exact same dimensions. The mass of the untreated material can then be subtracted from the mass of the head portion 52 in order to arrive at the mass of the adhesive composition itself. The mass of the adhesive composition can then be divided by the length L as shown in FIG. 7 in order to calculate the amount of adhesive composition in grams per linear meter. A similar analysis can be conducted in order to determine the amount of adhesive composition present in the tail portion 54 in grams per linear meter.

In general, the adhesive composition in the head portion 52 in grams per linear meter can be at least about 20%, such as at least about 30%, such as at least about 40%, such as at least about 50%, such as at least about 60%, such as at least about 70%, such as at least about 80%, such as at least about 90%, such as even at least about 100% greater than the amount of adhesive composition in grams per linear meter contained within the tail portion 54. For example, the adhesive composition in grams per linear meter in the head portion 52 can be greater than about 150%, such as greater than about 200% than the amount of adhesive composition in grams per linear meter contained in the tail portion 54. In general, the ratio of the amount of adhesive composition in grams per linear meter in the head portion 52 in comparison to the amount of adhesive composition in grams per linear meter in the tail portion 54 is less than about 50:1, such as less than about 20:1, such as less than about 10:1.

As shown in FIG. 6, the tail portion 54 can include a middle section 58 and an end section 60. The end section 60 can be located opposite the head portion 52. In one embodiment, the middle section 58 can have a substantially uniform basis weight while the end section 60 can have a gradually decreasing basis weight. For example, the basis weight of the middle section 58 can vary by no more than about 15%, such as by no more than about 10%, such as by no more than about 5% over the length of the middle section. The end section 60, on the other hand, can gradually decrease from the average basis weight of the middle section 58 to zero.

In general, the web of material 20 can comprise any suitable substrate for receiving the adhesive composition. The web of material 20, for instance, can comprise a single layer of material or can comprise a laminate. In one embodiment, the web of material 20 comprises a nonwoven web. For instance, the web of material 20 may comprise a spunbond web, a meltblown web, a coform web, a hydroentagled web, or the like. In one embodiment the web of material 20 can contain pulp fibers and may comprise a paper or tissue web. In another embodiment, the web of material 20 comprises a woven fabric or a knitted fabric. In still another alternative embodiment of the present disclosure, the web of material 20 can comprise a film. The film can be a single layer film or a multi-layer film.

In one embodiment, the web of material 20 may comprise a laminate comprised of multiple layers. In one embodiment, for instance, the web of material 20 may comprise a spunbond/meltblown/spunbond web.

The web of material 20 can be used to construct many different types of products. In one embodiment, for instance, the web of material 20 can be incorporated into an absorbent article. The adhesive composition is applied to the web during the process in order to attach a separate piece of material to the web for constructing a particular portion of the product. The absorbent article, for instance, may comprise a diaper, a training pant, a swim pant, an adult incontinence product, a feminine hygiene product, or the like. In one embodiment the adhesive composition may be applied to the web of material 20 in order to attach side panels to an absorbent article, such as elastic side panels. In an alternative embodiment, the adhesive composition may be used to attach fastener panels, such as hook and loop fasteners, to the material that serve as attachment devices for attaching the diaper to the wearer. In still another embodiment, the adhesive composition can be used to form a pocket within the absorbent article.

In another embodiment, the web of material 20 may be used to produce various other products in addition to absorbent articles. For instance, in one embodiment, the web of material 20 may be used to form packaging.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A material having an adhesive pattern for incorporating the material into a product comprising:
   a base web having a first surface and a second and opposite surface, the base web having a length direction and a width direction; and
   a pattern of treated discrete areas on the first surface of the base web, the treated discrete areas being formed from an adhesive composition, the treated discrete areas being parallel to each other and having a length extending in the length direction of the base web, each treated discrete area having a head portion and a tail portion, and wherein, when measured in grams per linear meter, greater amounts of the adhesive composition are present in the head portion than in the tail portion, wherein the head portion of each treated discrete area has a length and wherein the tail portion of each treated discrete area has a length and wherein the ratio of the length of the head portion to the length of the tail portion is from about 1:5 to about 1:40, wherein the adhesive pattern comprises a first end and a second end, wherein the pattern of treated discrete areas terminates at the head portion at the first end and terminates at the tail portion at the second end;

wherein the length of each treated discrete area is less than 80 mm.

2. The material as defined in claim 1, wherein the adhesive composition in grams per linear meter is present in the head portion in an amount that is at least 20% greater than the amount of adhesive composition contained in the tail portion in grams per linear meter.

3. The material as defined in claim 1, wherein the adhesive composition in grams per linear meter is present in the head portion in an amount that is at least 50% greater than the amount of adhesive composition contained in the tail portion in grams per linear meter.

4. The material as defined in claim 1, wherein the head portion of each treated discrete area has a width and wherein each tail portion of each treated discrete area has a width and wherein the maximum width of the head portion is larger than the maximum width of the tail portion.

5. The material as defined in claim 4, wherein the head portion is a circle or oval having a tail portion attached thereto, wherein the tail portion has a smaller width as compared to the head portion.

6. The material as defined in claim 1, wherein the material includes from 2 to 30 treated discrete areas.

7. The material as defined in claim 1, wherein the length of each treated discrete area is less than 60 mm.

8. The material as defined in claim 1, wherein the adhesive composition has a viscosity of from 500 cps to 20,000 cps when measured at a temperature of 350° F. (177° C.).

9. The material as defined in claim 1, wherein the adhesive composition comprises a hot melt adhesive.

10. The material as defined in claim 8, wherein the adhesive comprises a polyolefin polymer or a styrene block polymer.

11. The material as defined in claim 1, wherein the tail portion of each treated discrete area includes a middle section and an end section located opposite the head portion, the middle section having a substantially uniform basis weight while the end section has a gradually decreasing basis weight, wherein the middle section comprises a basis weight that varies by no more than about 15% and the end section comprises a basis weight that decreases from an average basis weight of the middle section to zero.

12. The material as defined in claim 1, wherein a weight ratio of the amount of adhesive composition contained in each head portion in comparison to the amount of adhesive composition contained in each tail portion is from 95:5 to 5:95.

13. The material as defined in claim 1, wherein the base web comprises a non-woven web.

14. The material as defined in claim 1, wherein the base web comprises a spunbond web, a meltblown web, a coform web, a hydroentangled web, a tissue web, or laminates thereof.

15. The material as defined in claim 1, wherein the base web comprises a laminate containing a meltblown web sandwiched in between a first spunbond web and a second spunbond web.

16. The material as defined in claim 1, wherein the treated discrete areas extend in a machine direction of the base web, the tail portion being positioned downstream from the head portion.

17. The material as defined in claim 1, wherein a weight ratio of the amount of adhesive composition in grams per linear meter contained in each head portion in comparison to the amount of adhesive composition in grams per linear meter contained in each tail portion is from 1.5:1 to about 50:1.

18. An absorbent article containing the material defined in claim 1.

19. An absorbent article as defined in claim 18, wherein the absorbent article comprises a diaper.

20. A process for producing a material having an adhesive pattern for incorporating the material into a product comprising the following steps:

conveying a base web adjacent to an adhesive applicator, the adhesive applicator comprising a nozzle, the base web having a first surface and a second and opposite surface, the base web having a length direction and a width direction;

contacting the first surface of the base web with the nozzle for a period of time; and applying a pattern of treated discrete areas on the base web, the treated discrete areas being parallel to each other and having a length extending in the length direction of the base web, the pattern of treated being applied to discrete areas on the first surface of the base web, the treated discrete areas being formed from an adhesive composition, each treated discrete area having a head portion and a tail portion, and wherein, when measured in grams per linear meter, greater amounts of the adhesive composition are present in the head portion than in the tail portion, wherein the head portion of each treated discrete area has a length and wherein the tail portion of each treated discrete area has a length and wherein the ratio of the length of the head portion to the length of the tail portion is from about 1:5 to about 1:40, wherein the adhesive pattern comprises a first end and a second end, wherein the pattern of treated discrete areas terminates at the head portion at the first end and terminates at the tail portion at the second end and wherein the length of each treated discrete area is less than 80 mm.

21. A process as defined in claim 20, further comprising the step of deflecting the base web with a web deflecting device such that the first surface of the base web contacts the nozzle, the web deflecting device contacting the web on a web contacting surface of the web deflecting device.

22. A process as defined in claim 20, wherein the base web remains in contact with the nozzle for about 4 milliseconds to about 1000 milliseconds during each contacting period.

* * * * *